United States Patent
Park et al.

(10) Patent No.: US 10,590,372 B2
(45) Date of Patent: *Mar. 17, 2020

(54) MULTI-STAGE PURIFICATION METHOD AND APPARATUS OF EXTRACELLULAR VESICLES USING AQUEOUS SOLUTION TWO-PHASE SYSTEM

(71) Applicant: POSTECH ACADEMY-INDUSTRY FOUNDATION, Pohang-si (KR)

(72) Inventors: Jae Sung Park, Pohang-si (KR); Hyun Woo Shin, Busan (KR)

(73) Assignee: POSTECH ACADEMY-INDUSTRY FOUNDATION, Pohang-si (KR)

(*) Notice: Subject to any disclaimer, the term of this patent is extended or adjusted under 35 U.S.C. 154(b) by 78 days.

This patent is subject to a terminal disclaimer.

(21) Appl. No.: 15/560,561

(22) PCT Filed: Mar. 3, 2016

(86) PCT No.: PCT/KR2016/002134
§ 371 (c)(1),
(2) Date: Sep. 22, 2017

(87) PCT Pub. No.: WO2016/153187
PCT Pub. Date: Sep. 29, 2016

(65) Prior Publication Data
US 2018/0105778 A1 Apr. 19, 2018

(30) Foreign Application Priority Data
Mar. 24, 2015 (KR) ........................ 10-2015-0040684

(51) Int. Cl.
*C12M 1/26* (2006.01)
*C12Q 1/68* (2018.01)
(Continued)

(52) U.S. Cl.
CPC ......... *C12M 1/264* (2013.01); *B01D 11/0488* (2013.01); *B01D 11/0492* (2013.01);
(Continued)

(58) Field of Classification Search
CPC .......... C12M 1/264; C12M 1/42; C12M 1/26; C12M 29/18; C12M 33/00; C12M 33/10;
(Continued)

(56) References Cited

U.S. PATENT DOCUMENTS 6,855,296 B1 * 2/2005 Baker ................ A61K 9/1277
264/4
8,802,362 B2 8/2014 Grippi et al.
(Continued)

FOREIGN PATENT DOCUMENTS

JP    2004-003920    1/2004
KR    10-0194075    6/1999
(Continued)

OTHER PUBLICATIONS

H. Shin et at., "Cancer-derived Extracellular Vesicle Isolation by Aqueous Two-Phase System", Abstract from the Third International Meeting of ISEV 2014, Journal of Extracellular Vesicles, vol. 3, Article 24214, Poster No. 09A-346, pp. 120, (2014).
(Continued)

*Primary Examiner* — Joseph W Drodge
(74) *Attorney, Agent, or Firm* — Lex IP Meister, PLLC

(57) ABSTRACT

This disclosure relates to a multi-stage method and apparatus for purifying extracellular vesicles using an aqueous two-phase system, in which extracellular vesicles mixed and contaminated with proteins can be isolated and purified in a large amount at high purity within a short time through a multi-stage purification process using an aqueous two-phase system, thereby removing 95% or more of proteins and obtaining high-purity extracellular vesicles, resulting in very
(Continued)

high processing efficiency compared to conventional techniques. In particular, the method of the disclosure does not require an expensive device or material such as an ultracentrifuge or an antibody, and can be performed at low cost and is thus economical and highly competitive. Furthermore, the extracellular vesicles thus isolated and purified can be employed in analysis methods such as RT-PCR or western blot, and can be utilized for research fields and disease diagnosis using the same.

7 Claims, 8 Drawing Sheets

(51) Int. Cl.

| | | |
|---|---|---|
| C12Q 1/24 | (2006.01) | |
| C12N 13/00 | (2006.01) | |
| G01N 33/53 | (2006.01) | |
| C12M 1/42 | (2006.01) | |
| C12N 5/00 | (2006.01) | |
| B01D 17/02 | (2006.01) | |
| B01D 11/04 | (2006.01) | |
| C12Q 1/6806 | (2018.01) | |
| G01N 33/535 | (2006.01) | |
| C12Q 1/686 | (2018.01) | |
| G01N 33/68 | (2006.01) | |

(52) U.S. Cl.
CPC .......... *B01D 17/0217* (2013.01); *C12M 1/26* (2013.01); *C12M 1/42* (2013.01); *C12N 5/0081* (2013.01); *C12N 13/00* (2013.01); *C12Q 1/24* (2013.01); *C12Q 1/6806* (2013.01); *C12Q 1/686* (2013.01); *G01N 33/535* (2013.01); *G01N 33/6803* (2013.01)

(58) Field of Classification Search
CPC ...... C12M 33/22; C12M 45/04; C12M 45/05; C12M 47/06; C12M 47/12; C12Q 1/6806; C12Q 1/686; C12Q 1/24; C12N 5/0081; C12N 13/00; C12N 5/00; G01N 33/6803; G01N 33/535; B01D 11/04; B01D 11/0419; B01D 11/0423; B01D 11/0488; B01D 11/0492; B01D 17/02; B01D 17/0217

USPC .............. 210/634, 639, 787, 789, 805, 806; 435/6.1, 6.14, 307.1, 308.1; 424/277.1
See application file for complete search history.

(56) References Cited

U.S. PATENT DOCUMENTS

| | | | | |
|---|---|---|---|---|
| 2003/0215845 A1* | 11/2003 | Bille | .................. | C12N 1/06 435/6.12 |
| 2012/0010390 A1* | 1/2012 | Van Alstine | ............ | C07K 1/14 530/388.1 |
| 2013/0177595 A1* | 7/2013 | Gho | .................. | A61K 47/10 424/277.1 |
| 2013/0195765 A1* | 8/2013 | Gho | .................. | A61K 9/5068 424/9.6 |
| 2013/0273544 A1 | 10/2013 | Vlassov et al. | | |
| 2013/0337440 A1* | 12/2013 | Antes | .................. | C12Q 1/6895 435/6.1 |
| 2014/0004539 A1* | 1/2014 | Simon | ............... | G01N 33/5306 435/7.92 |
| 2014/0030213 A1* | 1/2014 | Gupta | .................. | C07K 14/535 424/85.1 |
| 2014/0227712 A1* | 8/2014 | Horlitz | ................ | C12N 15/101 435/6.12 |

FOREIGN PATENT DOCUMENTS

| | | |
|---|---|---|
| KR | 10-0836171 | 6/2008 |
| KR | 10-0863466 | 10/2008 |
| KR | 10-2009-0064907 | 6/2009 |
| KR | 10-2012-0111788 | 10/2012 |
| KR | 10-2014-0050465 | 4/2014 |

OTHER PUBLICATIONS

D.M. Morre et al., "Aqueous Two-Phase Partition Applied to the Isolation of Plasma Membranes and Golgi Apparatus from Cultured Mammalian Cells", Journal of Chromatography B, vol. 743, pp. 377-387 (2000).
Scientific Program 2014 ISEV Meeting Wednesday Oral Presentations, Journal of Extracellular Vesicles, Third International Meeting of ISEV 2014, Rotterdam, The Netherlands, Apr. 30, 2014.

* cited by examiner

[FIG. 1]
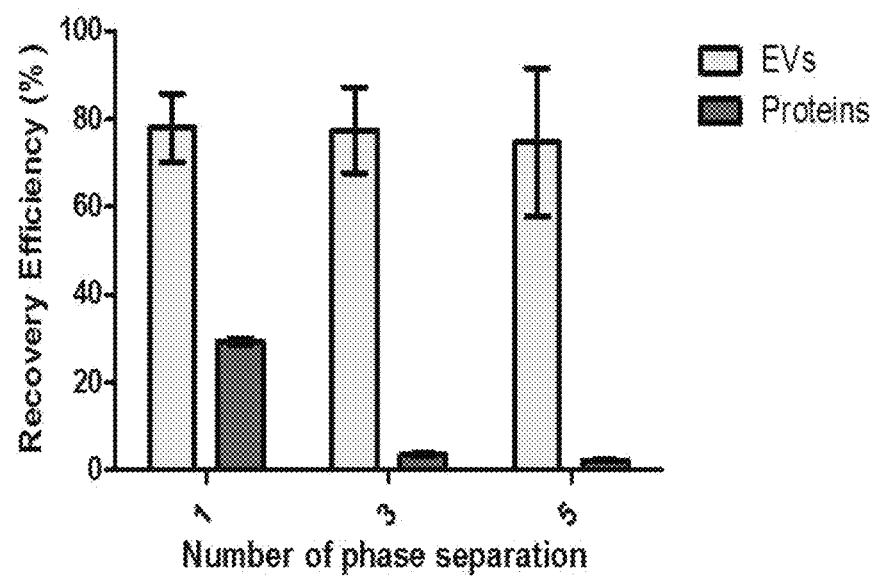

[FIG. 2]
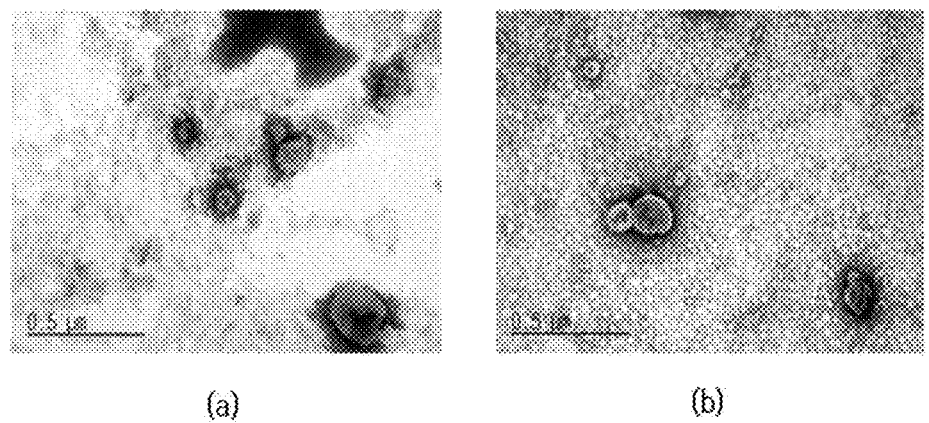
(a) (b)

[FIG. 3]
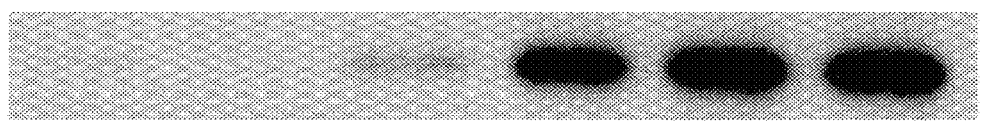
(a)
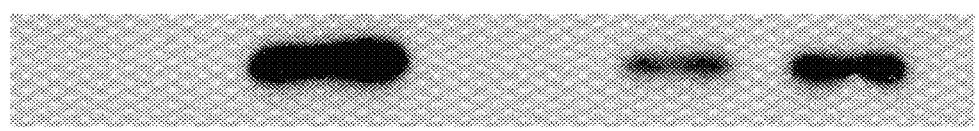
(b)

[FIG. 4]
GAPDH 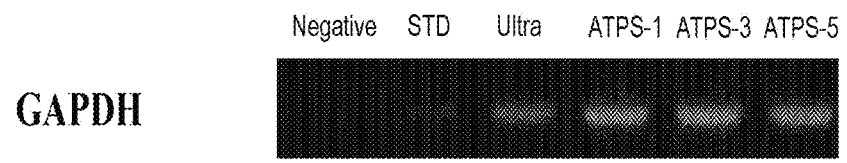
Melan A 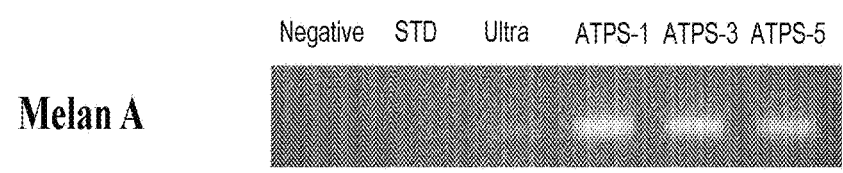

[FIG. 5]
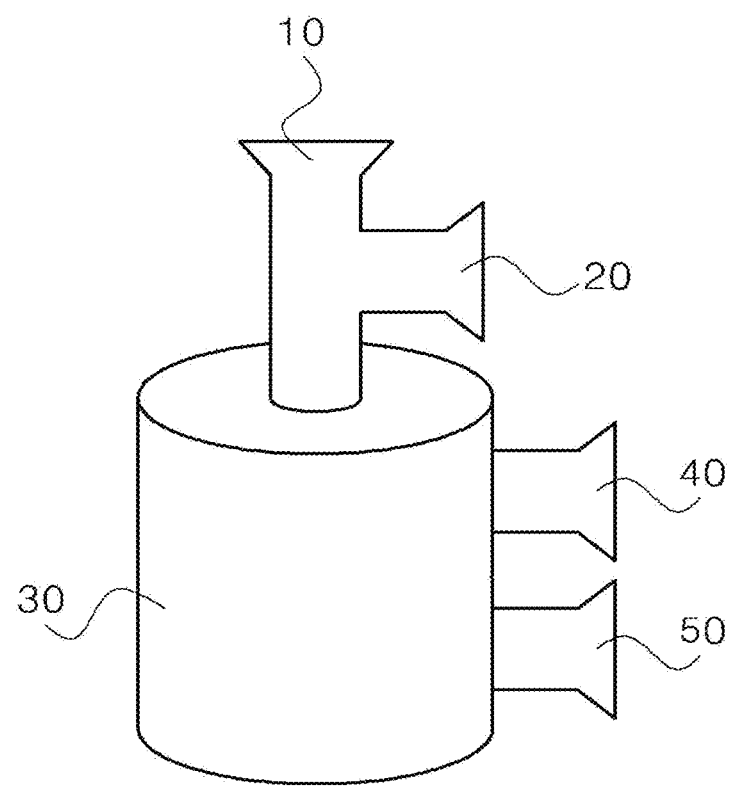

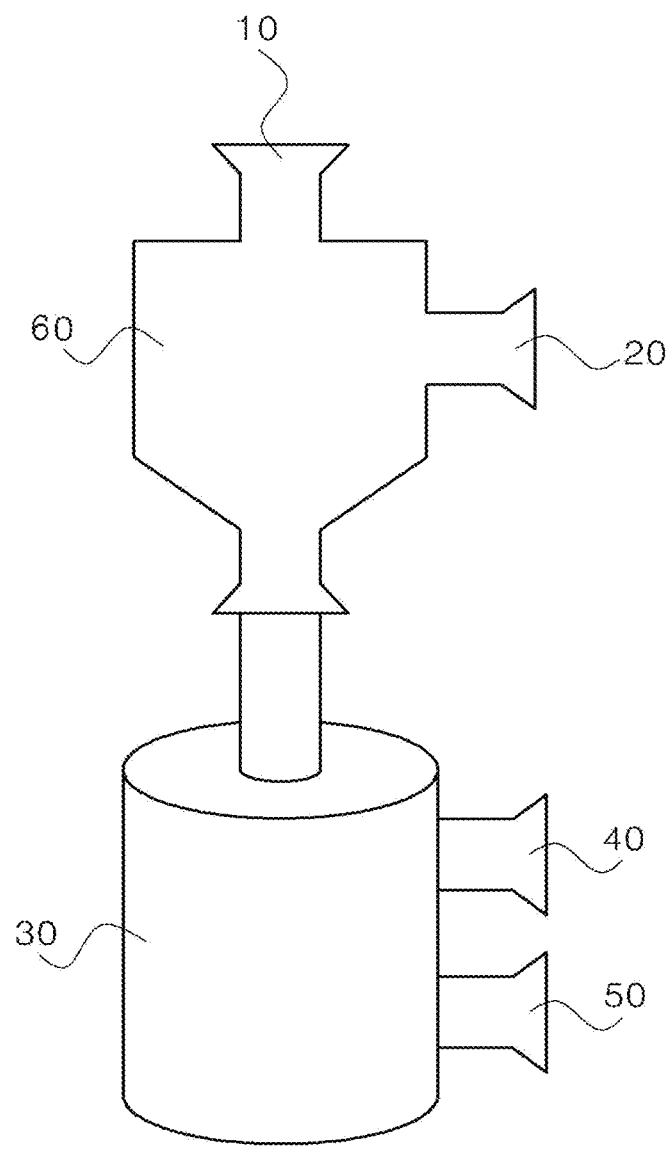
[FIG. 6]

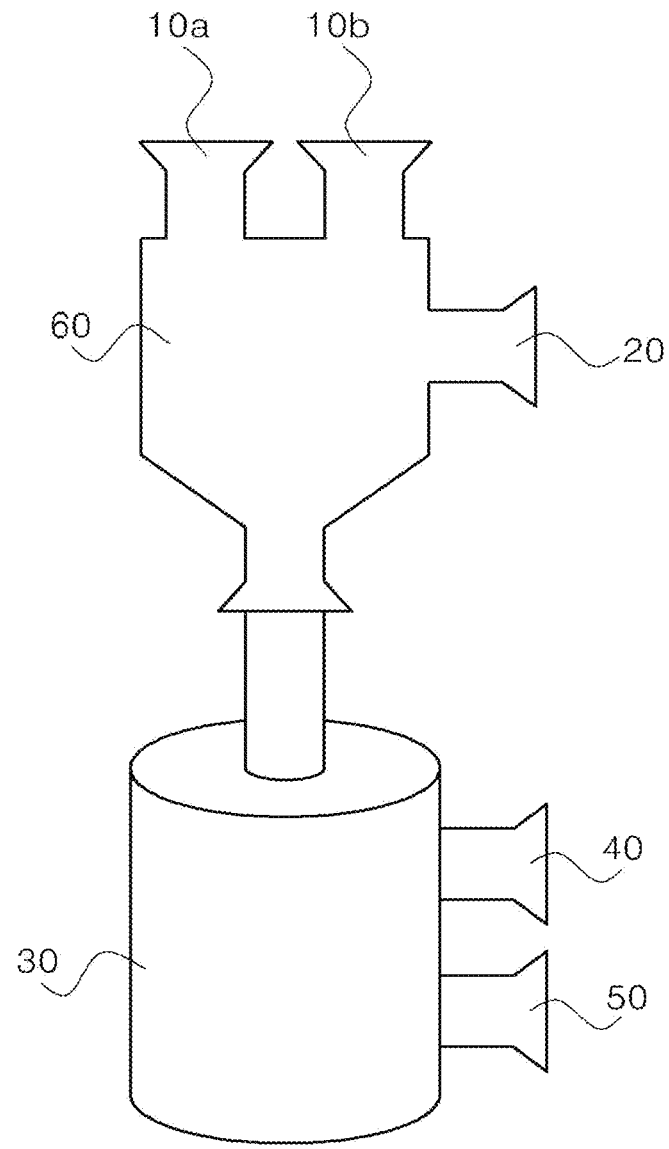
[FIG. 7]

[FIG. 8]
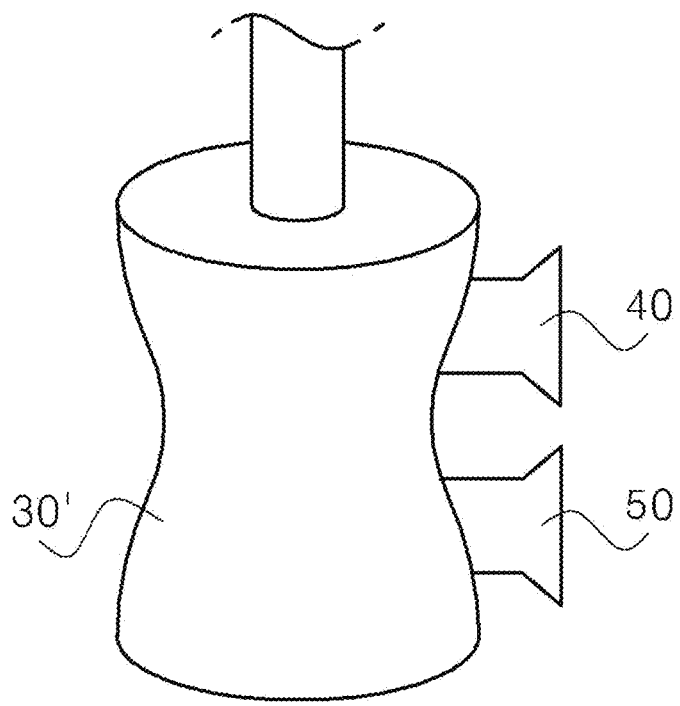

MULTI-STAGE PURIFICATION METHOD AND APPARATUS OF EXTRACELLULAR VESICLES USING AQUEOUS SOLUTION TWO-PHASE SYSTEM

TECHNICAL FIELD

The present invention relates to a multi-stage method and apparatus for purifying extracellular vesicles using an aqueous two-phase system, in which extracellular vesicles mixed and contaminated with proteins may be isolated and purified in a large amount at high purity within a short time through a multi-stage purification process using an aqueous two-phase system.

BACKGROUND ART

Extracellular vesicles include exosomes or microvesicles, having a size of about 50 to 1000 nm, and are thus useful as markers for diagnosing disease because they retain the characteristics of original cells.

Conventional techniques for isolating extracellular vesicles include ultracentrifugation, antibody isolation, a microfluidic method, and polymeric precipitation. Among these, the ultracentrifugation method is widely employed in the isolation of extracellular vesicles and is regarded as the most reliable by virtue of the simple principle therefor.

However, the case where extracellular vesicles are isolated using ultracentrifugation is problematic in that the yield of extracellular vesicles is low, the isolation time thereof is long, and expensive devices are required therefor.

The antibody isolation method, which adopts an antigen-antibody reaction, has high selectivity but makes it difficult to remove the antibody attached to vesicles and is unsuitable for mass production owing to the high price of the antibody.

The microfluidic method enables the rapid isolation of vesicles from a small amount of a sample by combining the antibody isolation with the microfluidic chip, but the application of the antibody to the microfluidic chip requires many preparation procedures.

The polymeric precipitation method enables the simple isolation of vesicles, but is disadvantageous in that all materials present in the sample precipitate and thus impurities such as proteins may be included therewith.

With the goal of overcoming the problems with conventional techniques, the present inventors have disclosed Korean Patent Application Publication No. 2014-0050465 regarding a microfluidic chip for isolating extracellular vesicles. The above patent is economically advantageous because extracellular vesicles are isolated from serum using an antibody-coated microfluidic chip, thus enabling extracellular vesicles to be isolated quickly and obviating the need for a laboratory, but is disadvantageous in terms of low yield, and hence, there are still problems to be solved in order to realize suitability for use in practical and economical diagnosis methods.

Meanwhile, the polymeric method decreases the solubility of body fluids to thereby precipitate extracellular vesicles, but requires a long incubation time, and moreover, proteins are precipitated therewith, thus resulting in low precipitate purity, making this method unsuitable for use in diagnosis.

DISCLOSURE

Technical Problem

Accordingly, the present disclosure has been made keeping in mind the problems encountered in the related art, and the present disclosure is intended to provide a multi-stage purification method of extracellular vesicles using an aqueous two-phase system, in which extracellular vesicles may be isolated and purified from an aqueous solution containing extracellular vesicles, thereby removing protein impurities and obtaining high-purity extracellular vesicles.

Technical Solution

Therefore, the present disclosure provides a multi-stage purification method of extracellular vesicles using an aqueous two-phase system, comprising the steps of: (a) mixing a first material and a second material with a body fluid or an aqueous solution containing extracellular vesicles; (b) subjecting the mixture to phase separation into an upper solution and a lower solution to give an aqueous two-phase system; (c) removing the upper solution including the first material from the aqueous two-phase system; (d) supplying and mixing the remaining lower solution with a new upper solution including the first material; and (e) performing the steps (b) to (d) at least once or two times and then recovering the extracellular vesicles from the lower solution.

The first material is selected from among water, polyethylene glycol, polyvinyl pyrrolidone, polyvinyl alcohol, and ficoll, and the second material is selected from among EOPO (ethylene oxide propylene oxide), dextran, a high-concentration salt, levan, poly(vinyl methyl ethyl ether), ammonium sulfate, sodium sulfate, magnesium sulfate, potassium phosphate, and sodium carbonate.

More specifically, when the first material is water, the second material is EOPO, and when the first material is polyethylene glycol, the second material may be selected from among dextran, levan, poly(vinyl methyl ethyl ether), ammonium sulfate, sodium sulfate, magnesium sulfate, potassium phosphate, and sodium carbonate. Also, when the first material is selected from among polyethylene glycol, polyvinyl pyrrolidone, polyvinyl alcohol, and ficoll, the second material is preferably dextran, and, more preferably, the first material is polyethylene glycol and the second material is dextran.

Also, the multi-stage purification method may further comprise controlling an attractive force or a repulsive force of molecules in the aqueous two-phase system by adding an additive to the aqueous two-phase system, after the step (a) and before the step (b).

The phase separation in the step (b) may be accelerated by performing centrifugation at 500~2,000×g-force, and the step (b) may further comprise applying ultrasonic waves or supplying microbubbles to the aqueous two-phase system.

The body fluid may be at least one selected from the group consisting of whole blood, serum, peritoneal fluid, breast milk, and urine.

The extracellular vesicles isolated by the multi-stage purification method of the present disclosure as described above may be employed in an analysis method such as ELISA, RT-PCR, western blot, proteomics, or genomics.

In addition, the present disclosure provides an apparatus for isolating extracellular vesicles using an aqueous two-phase system, comprising: an inlet 10 configured to introduce a first material and a second material, which constitute an aqueous two-phase system; a feeder 20 configured to feed a body fluid or an aqueous solution containing extracellular vesicles; a main body 30 connected to the inlet and the feeder and configured to perform phase separation by centrifuging the body fluid or the aqueous solution containing extracellular vesicles, the first material and the second material; a remover 40 for removing an upper solution including the first material after the phase separation; and a collector 50 configured to recover the extracellular vesicles from the main body 30.

The inlet 10 may include a first inlet 10a and a second inlet 10b so as to introduce the first material and the second material, respectively, and a mixer 60 may be disposed between the inlet 10 and the feeder 20 so as to mix the body fluid or the aqueous solution containing extracellular vesicles with the first material and the second material. As such, the mixer 60 is preferably equipped with a vibrator. Also, the main body 30 may further include a sonicator or a microbubble generator, and such a main body 30 has a cylindrical shape or a gourd shape.

Advantageous Effects

According to the present disclosure, a multi-stage purification method of extracellular vesicles using an aqueous two-phase system is capable of removing 95% or more of proteins and obtaining high-purity extracellular vesicles, thereby exhibiting very high processing efficiency compared to conventional techniques. In particular, the method of the disclosure does not require an expensive device or material such as an ultracentrifuge or an antibody, and can be performed at low cost and is thus economical. Therefore, the multi-stage purification method and apparatus is very competitive.

Furthermore, the extracellular vesicles isolated and purified according to the present disclosure can be employed in analysis methods such as RT-PCR or western blot, and can be utilized for research fields and disease diagnosis using the same.

DESCRIPTION OF DRAWINGS

FIG. 1 is a graph showing the results of recovery efficiency of extracellular vesicles and proteins depending on the frequency of phase separation;

FIGS. 2(a) and (b) show TEM (Transmission Electron Microscope) images of extracellular vesicles obtained by an ultracentrifugation process and a multi-stage purification process using an aqueous two-phase system according to the present disclosure, respectively;

FIGS. 3(a) and (b) show the image results of western blot analysis of extracellular vesicles obtained by the ultracentrifugation process and the multi-stage purification process using the aqueous two-phase system according to the present disclosure;

FIG. 4 shows the image results after RT-PCR of Melan A, which is mRNA of extracellular vesicles obtained by the multi-stage purification process using the aqueous two-phase system according to the present disclosure;

FIG. 5 shows a multi-stage purification apparatus of extracellular vesicles using an aqueous two-phase system according to the present disclosure;

FIG. 6 schematically shows the apparatus of FIG. 5, further including a mixer;

FIG. 7 schematically shows the apparatus of FIG. 6, the inlet of which is divided into two; and FIG. 8 schematically shows the multi-stage purification apparatus of extracellular vesicles using the aqueous two-phase system according to the present disclosure, in which the main body thereof is gourd-shaped.

MODE FOR INVENTION

Hereinafter, a detailed description will be given of technical features of the present disclosure with reference to the following examples and the appended drawings. However, the examples described in the present specification are merely preferred embodiments of the present disclosure, and do not represent all of the technical ideas of the present disclosure, and thus, it is to be understood that a variety of equivalents and modifications able to substitute therefor may be provided at the point of time at which the present disclosure is filed.

The present disclosure addresses a multi-stage purification method of extracellular vesicles using an aqueous two-phase system, comprising the steps of: (a) mixing a first material and a second material with a body fluid or an aqueous solution containing extracellular vesicles; (b) subjecting the mixture to phase separation into an upper solution and a lower solution to give an aqueous two-phase system; (c) removing the upper solution including the first material from the aqueous two-phase system; (d) supplying and mixing the remaining lower solution with a new upper solution including the first material; and (e) performing the steps b) to (d) at least once or two times and then recovering extracellular vesicles from the lower solution.

In the present disclosure, extracellular vesicles are vesicles which are produced in cells and secreted from the cells, examples of which include, but are not limited to, exosomes, microvesicles, and microparticles.

The combination of first material and second material (first material/second material) of the aqueous two-phase system according to the present disclosure preferably includes, but is not particularly limited to, any one selected from among water/EOPO (ethylene oxide propylene oxide), polyethylene glycol/dextran, polyethylene glycol/high-concentration salt, polyethylene glycol/levan, polyvinyl pyrrolidone/dextran, polyvinyl alcohol/dextran, ficoll/dextran, polyethylene glycol/poly(vinyl methyl ethyl ether), polyethylene glycol/ammonium sulfate, polyethylene glycol/sodium sulfate, polyethylene glycol/magnesium sulfate, polyethylene glycol/potassium phosphate, and polyethylene glycol/sodium carbonate. A variety of combinations of first material and second material may be used for the aqueous two-phase system.

The two materials, which are immiscible with each other and used to form the aqueous two-phase system, are most preferably polyethylene glycol/dextran, and extracellular vesicles may be characterized by being concentrated in the dextran phase, and the extracellular vesicles concentrated in the dextran phase may be isolated using a pipette, etc.

Here, polyethylene glycol has a molecular weight of 0.2~600 kDa and a concentration of 5~15 wt %, and dextran has a molecular weight of 15~2,000 kDa and a concentration of 1~10%. If the concentrations of polyethylene glycol and dextran are less than the above lower limits, an aqueous two-phase system is not formed. On the other hand, if the concentrations thereof are higher than the above upper limits, a long period of time is required to dissolve the polymers and surface tension is excessively high between the two phases, making it difficult to dissolve a third solute such as a body fluid.

After the step (a) and before the step (b), an additive may be added to the aqueous two-phase system, whereby attractive or repulsive force between molecules of the aqueous two-phase system may be controlled, thereby increasing the efficiency of isolation of extracellular vesicles. In particular, the potential of the aqueous two-phase system is preferably adjusted through addition of a salt. 0.05 mol $K_3PO_4$ is more preferably added.

In the step (b), the aqueous two-phase system may be subjected to centrifugation at 500~2,000 g-force for 5~15 min to thus further promote phase separation. If the centrifugation is performed at a level of less than 500×g-force, the isolation time may increase and thus the centrifugation may become meaningless. On the other hand, even if the g-value exceeds 2,000×g-force, there is no great change in the isolation time, which is undesirable.

Also, applying ultrasonic waves to the aqueous two-phase system or supplying microbubbles to the aqueous two-phase system may be further performed, thereby more effectively isolating proteins and extracellular vesicles trapped at the boundary of two phases.

The ultrasonic waves may be directly or indirectly applied to the solution, and preferably, this process is performed at an ultrasonic intensity of 200 W~400 W for 20~240 min. If the ultrasonic intensity exceeds 400 W, the temperature of the aqueous solution may drastically increase, thus degrading extracellular vesicles and proteins. On the other hand, if the ultrasonic intensity is less than 200 W, it is difficult to isolate proteins and extracellular vesicles trapped at the boundary of two phases. Also, if the ultrasonic processing time exceeds 240 min, the extent of isolation may not be further increased even for a long processing time. On the other hand, if the ultrasonic processing time is less than 20 min, the processing efficiency may decrease.

Removing the upper solution from the aqueous two-phase system subjected to phase separation and adding a new upper solution having no impurities therein are repeated to thereby isolate extracellular vesicles. As the number of such procedures that are repeated is increased, the purity of extracellular vesicles may increase, but the recovery efficiency may decrease. Thus, the number of procedures that are repeated is preferably 2~4.

In addition, according to the present disclosure, the purity of extracellular vesicles contaminated with proteins may be easily and efficiently increased, thus enabling various applications thereof to a variety of fields, such as disease diagnosis, vaccine research and therapy, and the like. More specifically, disease may be diagnosed by isolating extracellular vesicles from the body fluid and then measuring the expression level of genes present in the extracellular vesicles. Here, the body fluid may include, but is not particularly limited to, at least one selected from the group consisting of whole blood, serum, peritoneal fluid, breast milk, and urine. The disease may include, but is not particularly limited to, at least one selected from the group consisting of cancer, sepsis, arteriosclerosis, and rheumatoid arthritis.

The extracellular vesicles isolated by the multi-stage purification method using the aqueous two-phase system according to the present disclosure may be employed in analysis methods such as ELISA, RT-PCR, western blot, proteomics, or genomics.

Upon measurement of the expression level of a gene present in the extracellular vesicles, the gene may be mRNA, which shows variation in expression in response to stimuli, and the process of gene separation may be the same as the conventional process for separating genetic material from cells or tissue. More specifically, the gene is synthesized into cDNA using oligo(dT), followed by real-time PCR, but the template used for the real-time PCR is not limited to cDNA.

Here, the gene includes, but is not limited to, at least one selected from the group consisting of EDN1 (Endothelin-1), VCAM1 (Vascular cell adhesion molecule 1), ICAM1 (Intercellular adhesion molecule 1), SELE (Selectin E), NOS3 (Nitric oxide synthase 3), BMP4 (Bone morphogenetic protein 4), VWF (Von Willebrand factor), MPZ (Myelin protein zero), IRF1 (Interferon regulatory factor 1), TNF (Tumor necrosis factor), IL32 (Interleukin 32), CFLAR (CASP8 and FADD-like apoptosis regulator), CXCL10 (Chemokine (C-X-X motif) ligand 10), IL6 (Interleukin 6), ICK (Intestinal cell (MAK-like) kinase), TFAIP2 (Tumor necrosis factor, alpha-induced protein 2), ARHGAP8 (Rho GTPase-activating protein 8), and F3 (Coagulation factor HI).

A multi-stage apparatus for isolating and purifying extracellular vesicles using an aqueous two-phase system according to the present disclosure is illustrated in FIG. 5. More specifically, a first material and a second material for the aqueous two-phase system are introduced via an inlet 10, and a body fluid or an aqueous solution containing extracellular vesicles is fed via a feeder 20. The first material, the second material, and the body fluid or the aqueous solution containing extracellular vesicles are allowed to flow into a main body 30 connected to the inlet 10 and the feeder 20 and are thus subjected to phase separation through centrifugation, after which the upper solution including the first material is removed via a remover 40, and the extracellular vesicles obtained after performing multi-stage isolation and purification at least once or two times are recovered via a collector 50.

Also, a mixer 60 may be further disposed between the inlet 10 and the feeder 20, as shown in FIG. 6, so as to facilitate the mixing of the body fluid or the aqueous solution containing extracellular vesicles with the first material and the second material, and the mixer 60 is preferably equipped with a vibrator so as to achieve efficient mixing.

The main body 30 preferably further includes a sonicator or a microbubble generator, which functions to apply ultrasonic waves or generate microbubbles in order to effectively separate proteins and extracellular vesicles trapped at the boundary of two phases after phase separation.

The inlet 10 is preferably provided in the form of a first inlet 10a and a second inlet 10b for respectively introducing the first material and the second material, as illustrated in FIG. 7, and upon the preparation of the aqueous two-phase system, the concentrations of the first material and the second material may be adjusted depending on the kinds of polymer and body fluid.

The main body 30 may have a cylindrical shape, or may be gourd-shaped, as illustrated in FIG. 8. When the main body 30 is gourd-shaped, the phase boundary of the aqueous two-phase system is formed at the concave portion of the main body. In this case, the phase boundary is narrow and thus the trapped extracellular vesicles may be thickly formed to thereby facilitate the isolation thereof.

A better understanding of the present disclosure regarding the method of isolating the extracellular vesicles using the aqueous two-phase system will be given through the following examples, which are merely set forth to illustrate but do not represent all of the technical ideas of the present disclosure, and thus, it is to be understood that a variety of equivalents and modifications able to substitute therefor may be available at the point in time at which the present disclosure is filed.

Example 1

Preparation of Aqueous Two-Phase System for Isolation and Purification of Extracellular Vesicles In order to make an aqueous two-phase system, polyethylene glycol and dextran were dissolved in phosphate buffered saline (PBS) and prepared at respective concentrations of 10.5 wt % and 4.5 wt %. Thereafter, an aqueous solution containing extracellular vesicles was mixed with the mixed aqueous solution of polyethylene glycol and dextran and stirred at 4° C. for 3 hr using a shaker.

Example 2

Purification of Extracellular Vesicles Using Aqueous Two-Phase System

The aqueous two-phase system including extracellular vesicles, prepared in Example 1, was centrifuged at 1,000× g-force at 4° C. for 10 min to accelerate phase separation into a polyethylene glycol phase and a dextran phase. After the phase separation, the polyethylene glycol phase, corresponding to the upper solution except for the boundary layer, was removed, after which new polyethylene glycol was added in the same amount as the removed volume, followed by stirring and phase separation in the same manner as in Example 1.

The phase separation procedure was performed once, three times and five times. After the completion of respective multi-stage purification procedures, the recovery efficiency of proteins and extracellular vesicles was calculated based on Equation (1) below. The results are shown in FIG. 1.

Here, the amount of proteins was determined using a Bradford method and the amount of extracellular vesicles was measured from the amount of RNA.

Recovery efficiency ($E$)=(amount of proteins or extracellular vesicles in dextran layer)/(total amount of proteins or extracellular vesicles)   Equation (1)

As shown in FIG. 1, after the multi-stage purification once, three times, and five times, respective recovery efficiencies of extracellular vesicles were 77.9%, 77.4% and 74.7%. As the number of multi-stage purification procedures increased, the recovery efficiency of extracellular vesicles was slightly decreased without a large difference. However, respective protein recovery efficiencies were 29.4%, 3.6% and 2.4%, and thus the amount of recovered proteins was greatly decreased with an increase in the number of multi-stage purification procedures. Accordingly, when the number of multi-stage purification procedures is increased, the purity of extracellular vesicles can be confirmed to drastically increase.

Example 3

Analysis of Purified Extracellular Vesicles

In order to evaluate whether the extracellular vesicles purified in Example 2 are identical to the extracellular vesicles obtained using a conventional ultracentrifugation method and whether an assay may be performed through an analysis method using such extracellular vesicles, the following TEM, western blot, and RT-PCR were conducted.

a. Identification of Isolated Extracellular Vesicles (TEM)

The extracellular vesicles purified in Example 2 and the extracellular vesicles obtained through the ultracentrifugation method were observed using TEM (Transmission Electron Microscopy). The results are shown in FIG. 2.

As is apparent from the results of FIG. 2, the shape of extracellular vesicles obtained using the ultracentrifuge was the same as that of the extracellular vesicles purified by the present disclosure.

b. Western Blot

Western blot was conducted using a CD81 marker present in the extracellular vesicles.

In FIG. 3(a), STD indicates a standard comprising PBS and extracellular vesicles, which are mixed together, Ultra indicates ultracentrifugation, Ultra*5 indicates five times the amount of sample obtained by ultracentrifugation, and ATPS-1, ATPS-3 and ATPS-5 are samples obtained by performing phase separation once, three times and five times, as shown in Example 2. Here, to evaluate the recovery efficiency of extracellular vesicles, samples having the same volume were loaded, and thus the total protein amounts were different for individual samples.

In FIG. 3(b), samples having the same total protein content were loaded to evaluate the purity of extracellular vesicles. Thus, individual samples had different volumes.

When comparing the ultracentrifugation method with the multi-stage purification method of the present disclosure as shown in FIGS. 3(a) and 3(b), the extracellular vesicles obtained by the ultracentrifugation method had higher purity but much lower recovery efficiency, which is undesirable. Also, regardless of whether the number of phase separation procedures in the multi-stage purification method of the present disclosure was one, three or five, the results of recovery efficiency of extracellular vesicles were not greatly changed, but the purity thereof was increased with an increase in the number of phase separation procedures.

c. RT-PCR

The isolation and purification of extracellular vesicles without damage to RNA through the multi-stage purification method of the present disclosure were confirmed as follows.

Specifically, extracellular vesicles obtained from melanoma were mixed with serum protein to give a sample comprising extracellular vesicles contaminated with proteins, like biofluid. Thereafter, the above sample comprising extracellular vesicles was isolated and purified through the multi-stage purification method, after which mRNA known as Melan A was extracted and RT-PCR (reverse transcription PCR) was performed. The results thereof were compared with the results of RT-PCR on GAPDH, which is a housekeeping gene.

As is apparent from the results of RT-PCR of FIG. 4, Melan A and GAPDH were identical to each other, from which the extracellular vesicles were found to be isolated without damage to RNA through the multi-stage isolation and purification method according to the present disclosure (in FIG. 4, Negative indicates the case where there are no extracellular vesicles, and DW (distilled water) was used in lieu of the sample comprising extracellular vesicles).

As described hereinbefore, based on the test results of Examples 1 to 3, the multi-stage purification method of the present disclosure enables the isolation and purification of extracellular vesicles without damage to RNA, and the same extracellular vesicles as those obtained using the conventional ultracentrifugation method can be efficiently obtained at high purity. Upon the multi-stage purification, when the number of phase separation procedures is increased, the recovery efficiency of extracellular vesicles is slightly decreased but the recovery efficiency of proteins is greatly decreased, and thus the purity of extracellular vesicles can be confirmed to be gradually increased.

INDUSTRIAL APPLICABILITY

According to the present disclosure, upon isolation and purification of extracellular vesicles from an aqueous solution containing extracellular vesicles, a multi-stage purification method using an aqueous two-phase system is applied, thereby removing protein impurities and obtaining high-purity extracellular vesicles. The multi-stage purification method of extracellular vesicles using the aqueous two-phase system according to the present disclosure enables the removal of 95% or more of proteins and is capable of obtaining high-purity extracellular vesicles, and can thus exhibit very high processing efficiency compared to conventional purification methods. In particular, the method of the disclosure does not require expensive devices or materials such as an ultracentrifuge or an antibody, and is thus economical due to the low costs thereof. Also, the extracellular vesicles isolated and purified by the present disclosure can be employed in analysis methods such as RT-PCR or western blot, and can be utilized for research and disease diagnosis using the same, and are thus industrially applicable.

The invention claimed is:

1. A multi-stage purification method of extracellular vesicles using an aqueous two-phase system, comprising the steps of:
    (a) preparing a mixture by mixing a first material and a second material with (1) a body fluid containing extracellular vesicles and proteins, or (2) an aqueous solution containing extracellular vesicles mixed and contaminated with proteins;
    (b) separating the mixture to obtain an aqueous two phase system having an upper solution and a lower solution without ultracentrifugation;
    (c) removing the upper solution including the first material from the aqueous two-phase system;
    (d) supplying and mixing the lower solution with a new upper solution including a new quantity of the first material; and
    (e) performing the steps (b) to (d) at least two times and then recovering the extracellular vesicles from the lower solution,
    wherein the body fluid comprises at least one fluid selected from the group consisting of whole blood, serum, peritoneal fluid, breast milk, and urine,
    wherein the first material and the second material are immiscible with each other,
    wherein the first material is selected from the group consisting of polyethylene glycol, polyvinyl pyrrolidone, polyvinyl alcohol, and copolymers of sucrose and epichlorohydrin combinations thereof, and
    the second material is selected from the group consisting of EOPO (ethylene oxide propylene oxide), dextran, levan, poly(vinyl methyl ethyl ether), ammonium sulfate, sodium sulfate, magnesium sulfate, potassium phosphate, and sodium carbonate combinations thereof.

2. The multi-stage purification method of claim 1, wherein the second material is EOPO.

3. The multi-stage purification method of claim 1, wherein the first material is polyethylene glycol and the second material is selected from the group consisting of dextran, levan, poly(vinyl methyl ethyl ether), ammonium sulfate, sodium sulfate, magnesium sulfate, potassium phosphate, and sodium carbonate.

4. The multi-stage purification method of claim 1, wherein the first material is polyethylene glycol and the second material is dextran.

5. The multi-stage purification method of claim 1, further comprising controlling an attractive force or a repulsive force of molecules in the aqueous two-phase system by adding an additive to the aqueous two-phase system, after the step (a) and before the step (b).

6. The multi-stage purification method of claim 1, wherein the aqueous two phase system obtained in the step (b) is further subject to centrifugation at 500~2,000×g-force.

7. The multi-stage purification method of claim 1, wherein the step (b) further comprises applying ultrasonic waves or supplying microbubbles to the aqueous two-phase system.

* * * * *